(12) United States Patent
Hamel

(10) Patent No.: US 10,299,669 B2
(45) Date of Patent: May 28, 2019

(54) LIGHT-GUIDED JOINT ACCESS

(71) Applicant: Pivot Medical, Inc., Sunnyvale, CA (US)

(72) Inventor: Andrew J. Hamel, Sunnyvale, CA (US)

(73) Assignee: Pivot Medical, Inc., Sunnyvale, CA (US)

(*) Notice: Subject to any disclaimer, the term of this patent is extended or adjusted under 35 U.S.C. 154(b) by 217 days.

(21) Appl. No.: 15/168,683

(22) Filed: May 31, 2016

(65) Prior Publication Data

US 2016/0345816 A1 Dec. 1, 2016

Related U.S. Application Data

(60) Provisional application No. 62/167,393, filed on May 28, 2015.

(51) Int. Cl.
| | |
|---|---|
| A61B 1/317 | (2006.01) |
| A61B 1/06 | (2006.01) |
| A61B 1/07 | (2006.01) |
| A61B 17/34 | (2006.01) |
| A61B 90/30 | (2016.01) |
| A61B 90/00 | (2016.01) |

(52) U.S. Cl.
CPC ............ *A61B 1/317* (2013.01); *A61B 1/0676* (2013.01); *A61B 1/0684* (2013.01); *A61B 1/07* (2013.01); *A61B 17/3417* (2013.01); *A61B 17/3403* (2013.01); *A61B 2090/306* (2016.02); *A61B 2090/3945* (2016.02)

(58) Field of Classification Search
CPC .............................. A61B 1/317; A61B 1/0676
See application file for complete search history.

(56) References Cited

U.S. PATENT DOCUMENTS

| | | | | |
|---|---|---|---|---|
| 6,258,071 | B1* | 7/2001 | Brookes | A61B 17/3401 600/410 |
| 2005/0165418 | A1* | 7/2005 | Chan | A61B 17/0469 606/148 |
| 2012/0323079 | A1 | 12/2012 | Bakare et al. | |
| 2013/0204083 | A1* | 8/2013 | Schmieding | A61B 1/00078 600/104 |

* cited by examiner

*Primary Examiner* — Andrew Yang
(74) *Attorney, Agent, or Firm* — Pandiscio & Pandiscio

(57) ABSTRACT

A method for accessing the interior of a joint, wherein the joint comprises tissue which defines a boundary of the joint, the tissue comprising an interior surface facing toward the interior of the joint and an exterior surface facing away from the interior of the joint, the method comprising: providing a light-emitting needle assembly comprising a hollow needle having a light source at the distal end thereof; and observing the interior surface of the tissue from the interior of the joint as the needle approaches the exterior surface of the tissue.

54 Claims, 7 Drawing Sheets

LIGHT-GUIDED JOINT ACCESS

REFERENCE TO PENDING PRIOR PATENT APPLICATION

This patent application claims benefit of prior U.S. Provisional Patent Application Ser. No. 62/167,393, filed May 28, 2015 by Pivot Medical, Inc. and Andrew J. Hamel for LIGHT-GUIDED JOINT ACCESS, which patent application is hereby incorporated herein by reference.

FIELD OF THE INVENTION

This invention relates to surgical procedures in general, and more particularly to arthroscopic procedures.

BACKGROUND OF THE INVENTION

In arthroscopic procedures, access to the interior of a joint is generally provided through narrow cannulas which extend from the surface of the skin, through the intervening tissue, and into the interior of the joint. Arthroscopes and surgical instruments are then passed into and out of the joint space through the cannulas, whereby to enable so-called "keyhole" surgery. See FIG. 1.

It will be appreciated that, in most arthroscopic procedures, at least two portals are used, one to receive the arthroscope (which provides visualization of the internal surgical site) and one to receive the surgical instruments (which are used to perform the surgical procedure at the internal surgical site). In many cases, more than two portals are used.

It will also be appreciated that, depending on the joint, the specific number of portals used, and the exact locations of those portals, may be limited by the anatomy of the patient. By way of example but not limitation, in hip arthroscopy, it is common for two or three portals to be used, i.e., the first two portals being the so-called anterolateral portal (i.e., the "AL portal") and either the so-called anterior portal (i.e., the "A portal") or the so-called mid-anterior portal (i.e., the "MA portal"), while the third portal is typically the so-called distal anterolateral accessory portal (i.e., the "DALA portal").

When the first portal is created into the joint, the portal is generally created without the benefit of any internal visualization (i.e., because there is not yet an arthroscope positioned within the joint).

More particularly, when the first portal is created into the joint, a needle first penetrates from the skin through the intervening tissue structures and into the joint space, then a guidewire is placed through the needle's lumen into the joint space, next the needle is removed, and then a cannula with a blunt obturator is passed over the guidewire, through the skin, and down into the interior of the joint. Once the first cannula has been advanced into the interior of the joint, the obturator and guidewire are removed from the cannula, and then an arthroscope is advanced down the cannula so that its working end is disposed within the joint. Note that the arthroscope is generally releasably attached to the cannula while the arthroscope is deployed in the joint.

With the arthroscope deployed within the interior of the joint, the arthroscope may then be used to provide internal visualization during the creation of subsequent portals into the joint.

More particularly, in hip arthroscopy, the second portal is typically created by using a spinal needle to create a pathway into the joint, and then replacing the spinal needle with a cannula (i.e., in a manner similar to the creation of the first portal, whereby a guidewire is placed through the spinal needle, the spinal needle is removed, and then a cannula is advanced into position over the guidewire).

During creation of the second portal, the surgeon typically uses the arthroscope (which is already positioned within the joint via the first portal) to view the underside of the capsule of the joint and watch for the spinal needle (which is creating the second portal) engaging, and pushing inwardly on, the capsule, thereby creating an inward tenting effect on the capsule. This inward tenting effect on the capsule can then help the surgeon to confirm the proper positioning of the spinal needle relative to the capsule (i.e., to confirm the proper positioning of the second portal relative to the capsule) before the spinal needle is advanced through the capsule, i.e., by pushing harder on the spinal needle so that the spinal needle penetrates through the tough capsular tissue.

However, this inward tenting effect on the capsule can often be difficult to visualize (e.g., it may be a nominal tenting effect which can be difficult to detect vis-à-vis the adjacent capsule tissue), and/or it can be difficult to determine the precise needle location simply by viewing the tented tissue (since the tented tissue may have only a generalized curvature and may not present a distinct apex). Difficulty in visualizing a nominal tenting effect on the capsule can result in the surgeon advancing the spinal needle through the capsule at an undesirable location, potentially piercing and damaging tissue structures within the joint with the spinal needle. When this happens, the surgeon must withdraw the spinal needle from the joint, reposition the spinal needle against the exterior of the capsule, and then make another attempt to establish the second portal into the joint. This repositioning of the spinal needle consumes valuable operating room time. Also, incorrect advancement of the spinal needle into the joint creates the potential for the spinal needle to unintentionally pierce the labrum of the hip joint, or to unintentionally scrape the cartilage on the femoral head of the hip joint, either of which creates trauma to important anatomical structures and is a highly undesirable event.

Therefore, the surgeon needs a better way, when creating the second portal, to determine if the spinal needle is positioned at the correct location prior to piercing through the capsule.

SUMMARY OF THE INVENTION

The present invention provides the surgeon with a better way, when creating the second portal, to determine if the spinal needle is positioned at the correct location prior to piercing the capsule.

More particularly, in accordance with the present invention, a light source is disposed in the lumen of the spinal needle so that the light source emits light from the distal tip of the spinal needle. As the spinal needle pierces the surface of the skin, passes through the intervening tissue and advances to the outside surface of the capsule, the light from the light source penetrates through the capsule and can be viewed from the underside of the capsule (i.e., by the arthroscope already advanced into the interior of the joint via the first portal) so as to confirm proper positioning of the spinal needle before the spinal needle is advanced through the capsule.

In one preferred form of the present invention, there is provided a method for accessing the interior of a joint, wherein the joint comprises tissue which defines a boundary of the joint, the tissue comprising an interior surface facing toward the interior of the joint and an exterior surface facing away from the interior of the joint, the method comprising:

providing a light-emitting needle assembly comprising a hollow needle having a light source at the distal end thereof; and observing the interior surface of the tissue from the interior of the joint as the needle approaches the exterior surface of the tissue.

In another preferred form of the present invention, there is provided apparatus for providing access to the interior of a joint, the apparatus comprising:

a light-emitting needle assembly comprising:

a hollow needle having a distal end, a proximal end and a lumen extending therebetween; and a light unit comprising a light fiber comprising a distal end and a proximal end;

wherein the light fiber of the light unit is disposed at least partially within the hollow needle so that the distal end of the light fiber is disposed adjacent the distal end of the hollow needle, whereby when light is introduced into the proximal end of the light fiber, light will be emitted from the distal end of the light fiber and hence from the distal end of the hollow needle.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

The present invention provides the surgeon with a better way, when creating the second portal, to determine if the spinal needle is positioned at the correct location prior to piercing the capsule.

Light-Emitting Spinal Needle Assembly

Figure 3:
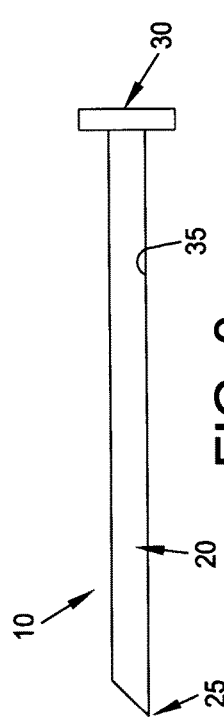
FIG. 3 is a schematic view showing a spinal needle used in the light-emitting spinal needle assembly shown in FIG. 2.
Figure 4:
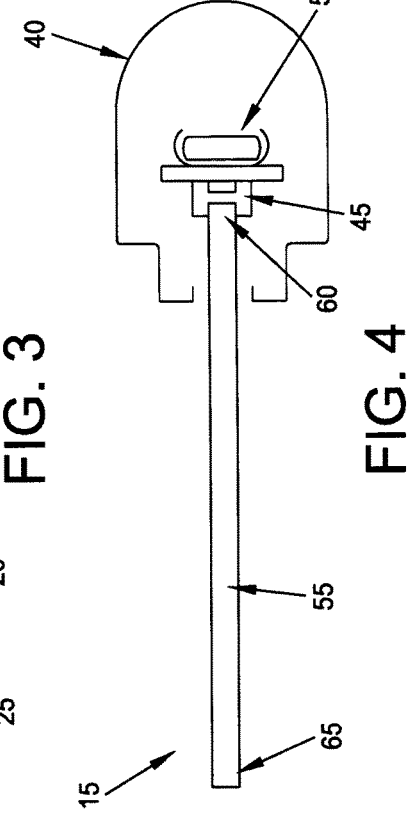
FIG. 4 is a schematic view showing a light unit used in the light-emitting spinal needle assembly shown in FIG. 2.

More particularly, in one preferred form of the invention, there is provided a light-emitting spinal needle assembly 5 (FIG. 2) which generally comprises a spinal needle 10 (FIG. 3) and a light unit 15 (FIG. 4).

Spinal needle 10 (FIG. 3) is a conventional spinal needle (or similar needle) comprising a shaft 20 having a distal end 25 terminating in a sharp point, a proximal end 30 and a lumen 35 extending therebetween.

Light unit 15 (FIG. 4) preferably comprises a handle 40 housing light-emitting element 45 (e.g., an LED) which is powered by a portable power supply 50 (e.g., a battery). A light fiber 55 extends distally out of handle 40. More particularly, light fiber 55 comprises a proximal end 60 disposed adjacent to light-emitting element 45 and a distal end 65 for insertion into spinal needle 10 as will hereinafter be discussed. Light fiber 55 is configured so that light introduced into the proximal end 60 of light fiber 55 is delivered to, and is emitted from, distal end 65 of light fiber 55.

Figure 1:
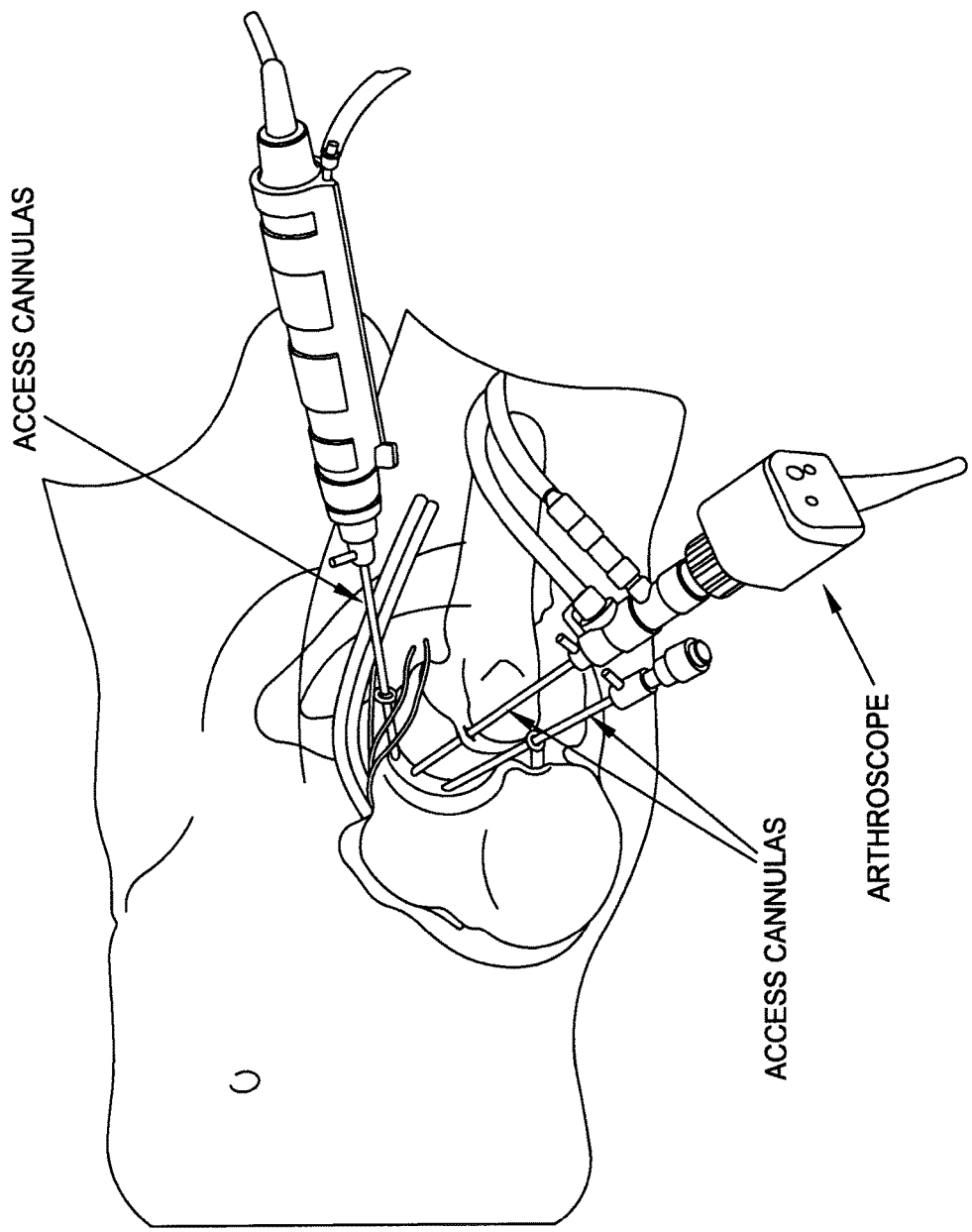
FIG. 1 is a schematic view showing a typical arthroscopic procedure.
Figure 2:
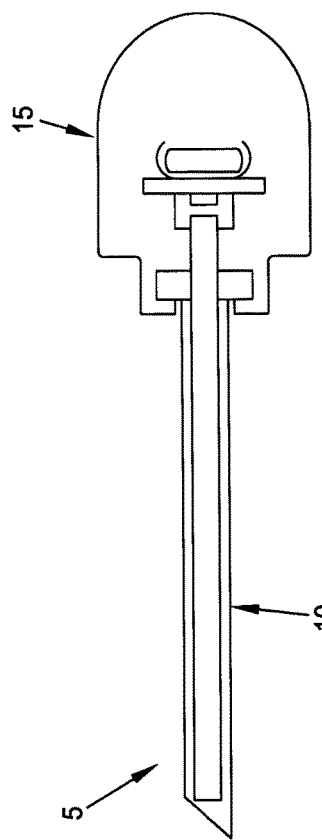
FIG. 2 is a schematic view showing a light-emitting spinal needle assembly formed in accordance with the present invention.

Light fiber 55 of light unit 15 (FIG. 4) is disposed within spinal needle 10 (FIG. 3) so as to together form light-emitting spinal needle assembly 5 (FIG. 2). More particularly, light fiber 55 of light unit 15 extends through lumen 35 of spinal needle 10 so that distal end 65 of light fiber 55 is positioned at (or near) the distal end 25 of spinal needle 10, with proximal end 30 of spinal needle 10 mating with handle 40 of light unit 15, whereby to form the complete light-emitting spinal needle assembly 5. In this way, the distal end of light fiber 55 acts as a light source for emitting light from the distal end of light-emitting spinal needle assembly 5. Distal end 65 of light fiber 55 may be shaped so as to form a lens in order to project the light emitted by light fiber 55 (e.g., shaped as a convex lens in order to provide a diverging light beam) and/or one or more lenses may be provided at the distal end of light fiber 55 in order to project the light emitted by light fiber 55.

In one preferred form of the invention, proximal end 30 of spinal needle 10 mates with handle 40 of light unit 15 via a luer lock-type connector or another type of connector.

Note that in one preferred form of the invention, distal end 65 of light fiber 55 is substantially flush with, or minimally proximal to, the distal end of spinal needle 10 so that the distal end of the light fiber acts as a stylet for the hollow spinal needle, whereby to prevent tissue coring (e.g., in a manner similar to how a stylet is normally used with a spinal needle). In any case, however, distal end 65 of light fiber 55 is disposed so that light emitted by the distal end of the light fiber 55 projects out the distal end of spinal needle 10.

Thus it will be seen that light-emitting spinal needle assembly 5 generally comprises a spinal needle having a light fiber disposed in its lumen, with the light fiber being illuminated at its proximal end with a light-emitting element so that light is emitted from the distal tip of the spinal needle.

The light provided by light unit 15 is preferably a high-intensity, "tight beam" light emission so that a point source of light is visible through the capsule (as opposed to a low-intensity, "diffused" light emission which would be difficult to see through the capsule). The light provided by light unit 15 can be of any wavelength or wavelengths capable of being detected by an arthroscope, but the light preferably comprises one or more infrared (IR) or near-infrared (near-IR) wavelengths, since IR and near-IR wavelengths are generally more effective in penetrating tissue than shorter wavelengths.

Using the Light-Emitting Spinal Needle Assembly to Provide Light-Guided Joint Access Light-emitting spinal needle assembly 5 may be used to provide light-guided joint access.

More particularly, a first portal is formed into the joint and then an arthroscope is advanced through the first portal and into the interior of the joint. Then, with light fiber 55 disposed within lumen 35 of spinal needle 10, and with light emitting element 45 energized so that light is emitted from distal end 25 of spinal needle 10, the spinal needle is advanced through the skin, passed through the intervening tissue and placed up against the outside of the capsule. Note that the surgeon can "feel" the engagement of the spinal needle with the capsule due to the tactile feedback experienced by the surgeon during advancement of the spinal needle, inasmuch as the capsule comprises significantly denser tissue than the intervening tissues (such as muscle and fat) and hence provides greater resistance to penetration. The light emitted from the distal end of the spinal needle will pass through the capsule and can (when the spinal needle is correctly positioned against the capsule) be viewed from the underside of the capsule (i.e., by the arthroscope previously advanced into the interior of the joint via the first portal). See FIG. 5.

Figure 5:
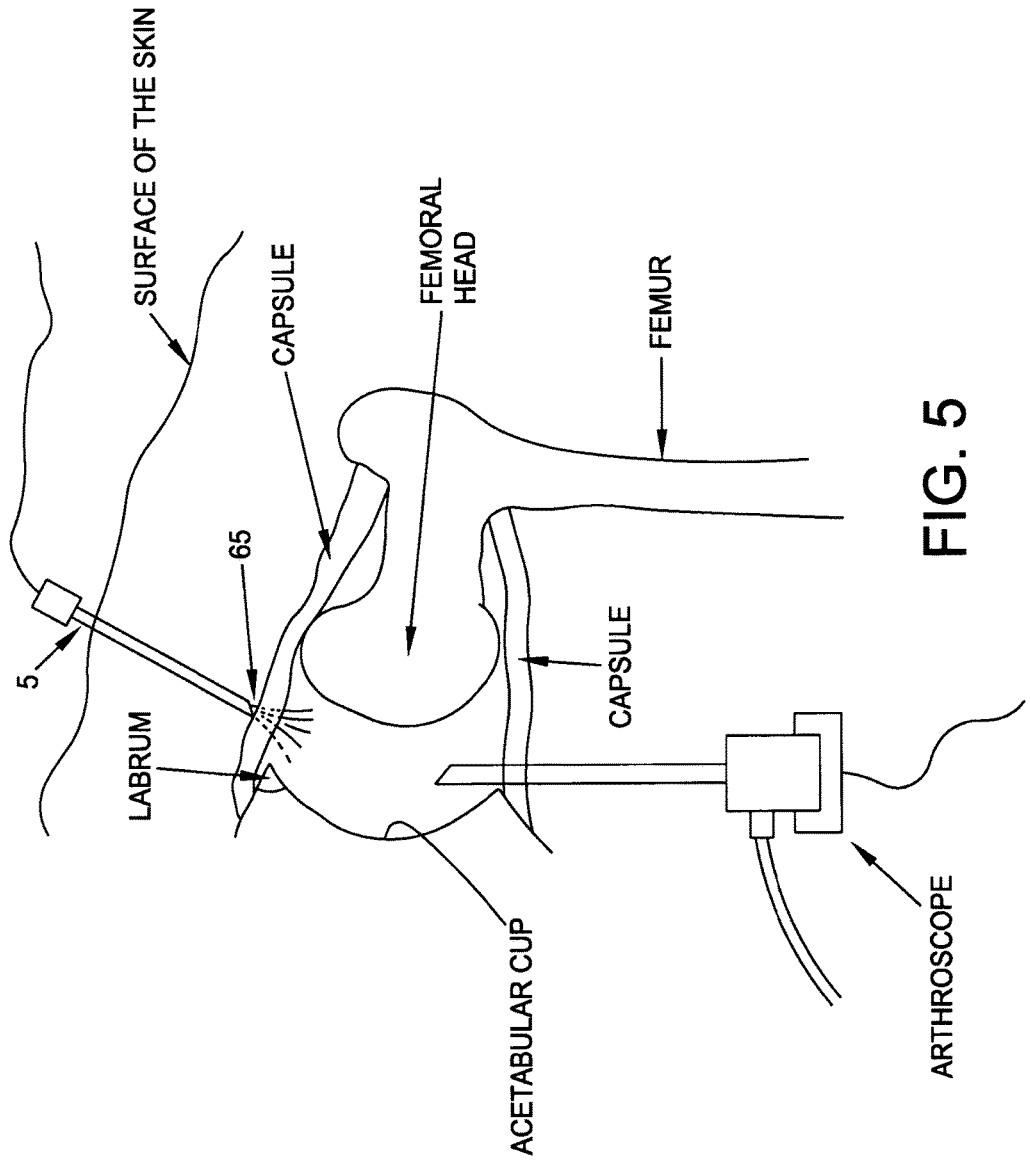
FIG. 5 is a schematic view showing a light-emitting spinal needle assembly engaging the outer surface of the capsule of a joint.

If the spinal needle is correctly located in the gap between the femoral head and the labrum, such as is shown in FIG. 5, the spinal needle is advanced through the capsule and into the interior of the joint. See FIG. 6.

Figure 7:
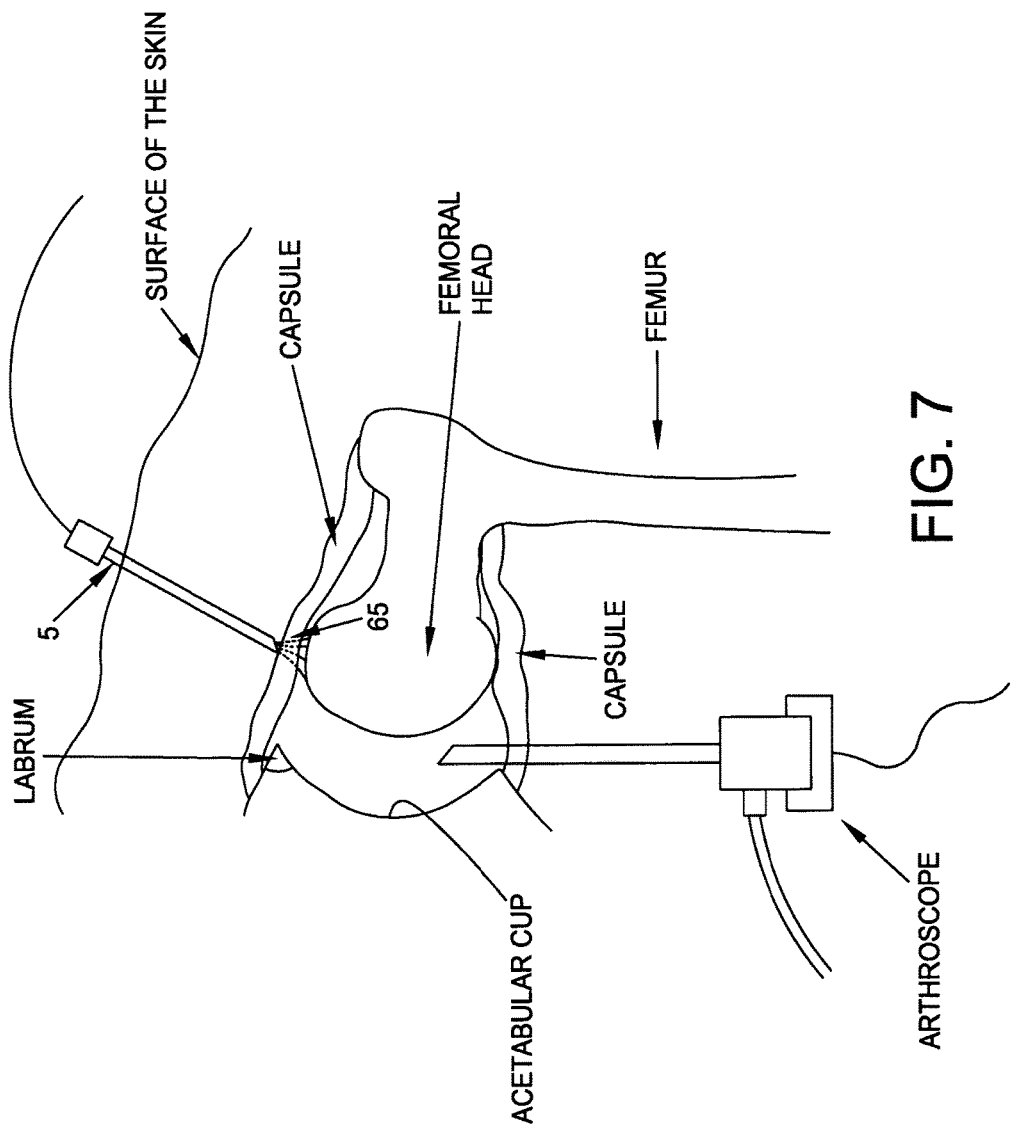
FIG. 7 is a schematic view showing a light-emitting spinal needle assembly oriented toward the femoral head as it engages the outer surface of the capsule of a joint.
Figure 8:
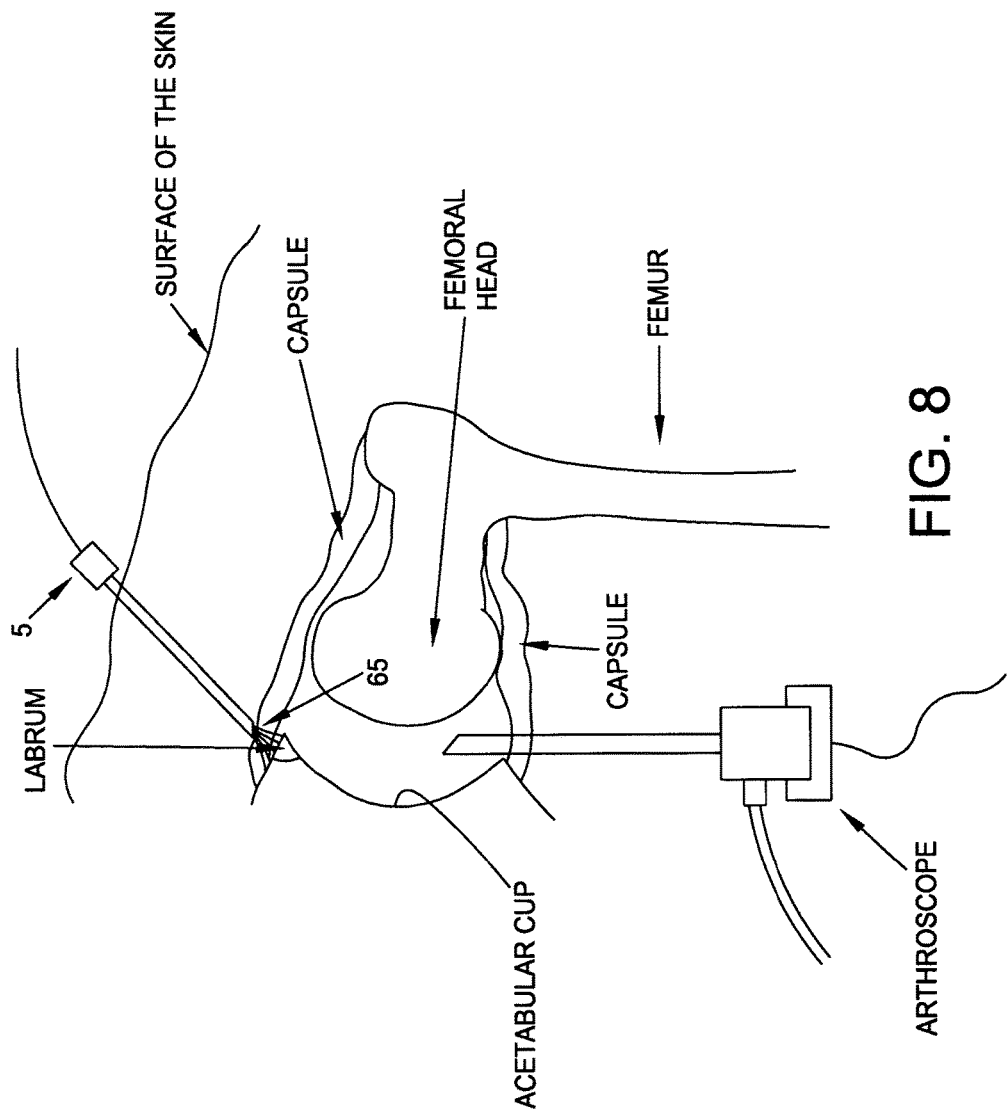
FIG. 8 is a schematic view showing a light-emitting spinal needle assembly oriented toward the labrum as it engages the outer surface of the capsule of a joint.

However, if the spinal needle is not located in the gap between the femoral head and the labrum (see, for example, FIG. 7, where the spinal needle is oriented towards the femoral head, and FIG. 8, where the spinal needle is oriented toward the labrum), the surgeon will not see the light from the light unit disposed in the spinal needle. The surgeon will, therefore, know that the spinal needle is not positioned in the correct location, and the surgeon will reposition the spinal needle on the outside of the capsule until the light emitted from the distal end of the spinal needle can be seen with the arthroscope (FIG. 5). Many times this can be done without withdrawing the spinal needle all the way back out of the skin, inasmuch as the skin and the intervening tissue are fairly elastic and typically permit such repositioning of the spinal needle.

Figure 6:
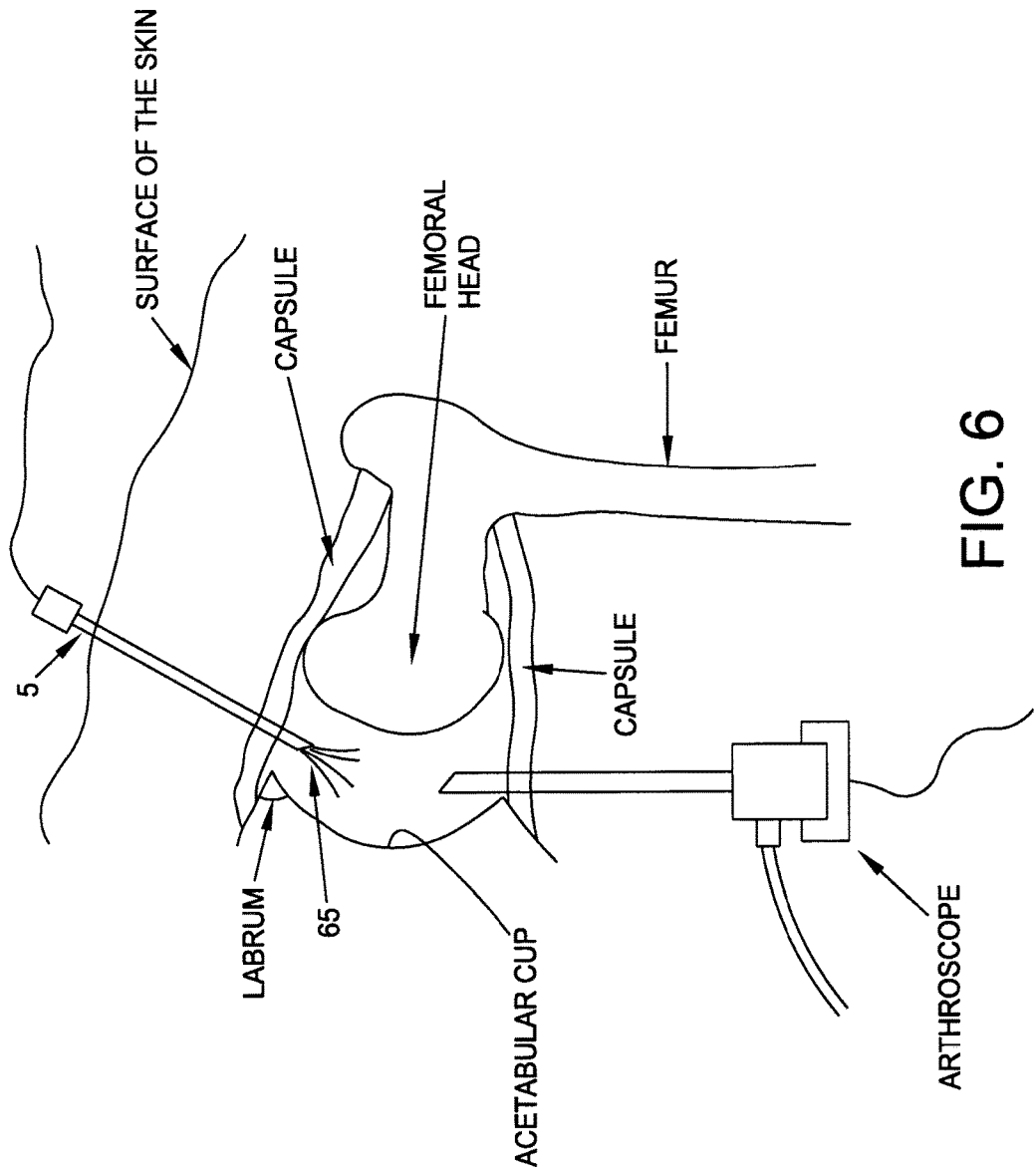
FIG. 6 is a schematic view showing a light-emitting spinal needle assembly penetrating the capsule of a joint.

Once it is confirmed that the light emitted from the distal end of the spinal needle is in the preferred location (e.g., in the gap between the femoral head and the labrum, such as shown in FIG. 5), the surgeon will know that the spinal needle is positioned in the correct location and the surgeon will proceed to advance the spinal needle through the capsule (FIG. 6). Light unit 15 is then disconnected from spinal needle 10 and removed. A guidewire is then advanced into the spinal needle, and then the spinal needle is replaced with a cannula, etc., whereby to complete creation of the second portal into the joint.

It will be appreciated that by providing the spinal needle with a light source which is visible through the capsule, the spinal needle may be passed through the capsule with increased precision, since the light source provides a visually distinct and highly accurate indication of needle position prior to passing the needle through the capsule.

It should be appreciated that it is not necessary for the distal end of light-emitting spinal needle assembly 5 to be in actual engagement with the outer surface of the capsule in order for the light emitted by the distal end of the spinal needle to be detected by an arthroscope located within the interior of the joint—in general, as long as the assembly has a light source of sufficient intensity, the approaching spinal needle can be detected prior to its actual engagement with the outer surface of the capsule. This feature allows the orientation of the spinal needle to be adjusted earlier in its advancement.

Figure 9:
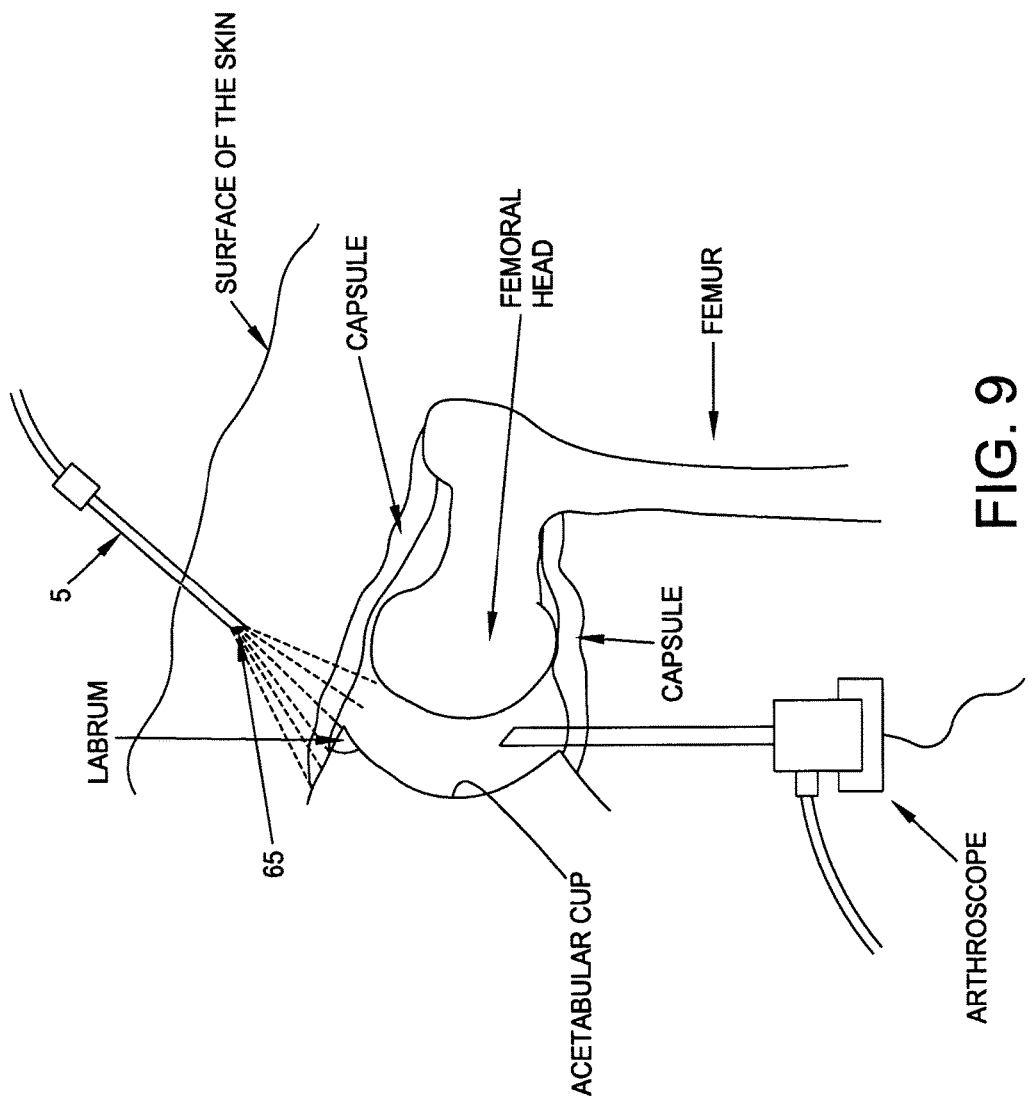
FIG. 9 is a schematic view showing a light-emitting spinal needle assembly oriented toward the labrum prior to engagement with the outer surface of the capsule of a joint.

By way of example but not limitation, if the spinal needle is located off to the side of the gap between the femoral head and the labrum, some light from the light source may still be visible to the arthroscope while the spinal needle is displaced from the capsule, so that the surgeon will know in which direction the spinal needle should be re-positioned. For example, if the spinal needle is positioned over the labrum but is not in the gap between the labrum and femoral head (FIG. 9), a glow of light may be visible from the distal end of the spinal needle; this indicates the location of the spinal needle to the surgeon, so that the surgeon can then re-position the spinal needle in the desired location. In other words, where the spinal needle has a light source within the needle, the surgeon will do less "searching" for the desired location than where the spinal needle lacks a light source within the needle, thereby reducing the time needed to establish the portal. Additionally, a properly-positioned spinal needle having a light source will always be visible through the capsule and thus be a more reliable means to identify needle location prior to piercing the capsule, thereby reducing the chance that the spinal needle either penetrates the labrum or unintentionally scrapes the cartilage on the femoral head.

Additional Aspects of the Present Invention

Additionally, the light provided by light unit 15 can be continuous light or flashing/strobing light.

The "spot size" of the light source provided at the distal end of light fiber 55 can be variable such that the "spot size" of the light source can go from broad to focused (e.g., like a laser pointer) as the spinal needle gets closer to the joint.

Also, it will be appreciated that light-emitting element 45 (e.g., an LED) might be powered by an external power source (e.g., a power cable extending from a power console or from a wall plug). Alternatively, the light-emitting element 45 supplying light to the proximal end of light fiber 55 might not be carried by handle 40, e.g., light-emitting element 45 might be housed in a separate light source console and coupled to the proximal end of light fiber 55 by an optical cable. In this form of the invention, light fiber 55 is still connected to proximal end 30 of spinal needle 10 such that light fiber 55 can be disconnected from spinal needle 10 after spinal needle 10 has penetrated the capsule.

It will be appreciated that in the foregoing example, and as seen in FIGS. 1 and 5-9, the first portal is preferably created at the AL portal, and the second portal is preferably created at either the A portal or the MA portal.

Further, it will also be appreciated that the present invention can be utilized to create portals into other joints, e.g., the shoulder joint, the knee joint, etc.

Modifications

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. A method for accessing the interior of a joint, wherein the joint comprises tissue which defines a boundary of the joint, the tissue comprising an interior surface facing toward the interior of the joint and an exterior surface facing away from the interior of the joint, the method comprising:

while moving a light-emitting element from the exterior of the joint towards the joint, observing the interior surface of the tissue of the joint to detect the location of the light-emitting element relative to the interior of the joint.

2. A method according to claim 1 wherein the light-emitting element comprises an elongated object with a tissue-penetrating tip.

3. A method according to claim 2 wherein the elongated object comprises a distal end, a proximal end and a lumen extending between the distal end and the proximal end, and further wherein the light-emitting element is at least partially disposed within the lumen of the elongated object.

4. A method according to claim 3 wherein the light-emitting element comprises a light fiber comprising a distal end and a proximal end.

5. A method according to claim 4 wherein the distal end of the light fiber is disposed adjacent to the distal end of the elongated object.

6. A method according to claim 5 wherein the distal end of the light fiber acts as an obturator for the distal end of the elongated object so as to prevent tissue coring.

7. A method according to claim 4 wherein light from the light-emitting element enters the proximal end of the light fiber and is emitted from the distal end of the light fiber.

8. A method according to claim 7 wherein the light-emitting element comprises an LED.

9. A method according to claim 7 wherein the light-emitting element emits light having a wavelength in at least one of the infrared (IR) and near-infrared (near-IR) wavelengths.

10. A method according to claim 3 wherein the light-emitting element comprises a handle, and further wherein the handle is releasably securable to the elongated object.

11. A method according to claim 3 wherein the orientation of the elongated object approaching the exterior surface of the tissue is modified as the elongated object approaches the exterior surface of the tissue based upon observation of the light emitted from the light-emitting element.

12. A method according to claim 11 wherein, after the elongated object has advanced through the tissue, the light-emitting element is removed from the elongated object without removing the elongated object from the tissue.

13. A method according to claim 12 comprising the steps of:
removing the light-emitting element from tissue;
placing a guidewire through the elongated object;
removing the elongated object from the tissue;
advancing a cannulated device over the guidewire; and
removing the guidewire from the cannulated device.

14. A method according to claim 1 wherein an arthroscope is used to observe the interior surface of the tissue from the interior of the joint as the light-emitting element approaches the exterior surface of the tissue.

15. A method according to claim 1 wherein the tissue comprises a capsule.

16. A method for accessing the interior of a joint, wherein tissue defines a boundary of the joint, the tissue comprising an interior surface facing toward the interior of the joint and an exterior surface facing away from the interior of the joint, the method comprising:
providing a light-emitting needle assembly comprising a needle and a light unit carried by the needle, wherein the needle comprises a distal end and a proximal end, and wherein the light unit comprises a light-emitting element for delivering light to the distal end of the needle; and
observing the interior surface of the tissue from the interior of the joint to detect light from the light unit carried by the needle as the distal end of the needle is advanced from the exterior of the joint toward the interior of the joint.

17. A method according to claim 16 wherein the tissue comprises a capsule.

18. A method according to claim 16 wherein the needle comprises a lumen extending between the distal end and the proximal end, and further wherein the light unit is at least partially disposed within the lumen of the needle.

19. A method according to claim 18 wherein the light unit comprises a light fiber comprising a distal end and a proximal end, and further wherein the light fiber is at least partially disposed within the lumen of the needle.

20. A method according to claim 18 wherein the light unit comprises a handle, and further wherein the handle is releasably securable to the needle.

21. A method according to claim 19 wherein the distal end of the light fiber is disposed adjacent to the distal end of the needle.

22. A method according to claim 21 wherein the distal end of the light fiber acts as an obturator for the distal end of the needle so as to prevent tissue coring.

23. A method according to claim 19 wherein the light-emitting element is disposed adjacent to the proximal end of the light fiber, such that light from the light-emitting element enters the proximal end of the light fiber and is emitted from the distal end of the light fiber.

24. A method according to claim 23 wherein the light-emitting element comprises an LED.

25. A method according to claim 23 wherein the light-emitting element emits light having a wavelength in at least one of the infrared (IR) and near-infrared (near-IR) wavelengths.

26. A method according to claim 16 wherein an arthroscope is used to observe the interior surface of the tissue from the interior of the joint as the needle approaches the exterior surface of the tissue.

27. A method according to claim 16 wherein the orientation of the needle approaching the exterior surface of the tissue is modified as the needle approaches the exterior surface of the tissue based upon observation of the light emitted from the distal end of the light-emitting needle assembly.

28. A method according to claim 27 wherein, after the light-emitting needle assembly has advanced through the tissue, the light unit is removed from the light-emitting needle assembly without removing the needle from the tissue.

29. A method according to claim 28 comprising the steps of:
removing the light unit from tissue;
placing a guidewire through the needle;
removing the needle from the tissue;
advancing a cannulated device over the guidewire; and
removing the guidewire from the cannulated device.

30. A method for accessing the interior of a joint, wherein the joint comprises tissue which defines a boundary of the joint, the tissue comprising an interior surface facing toward the interior of the joint and an exterior surface facing away from the interior of the joint, the method comprising:
providing a light-emitting needle assembly comprising a hollow needle having a light source at the distal end thereof; and observing the interior surface of the tissue from the interior of the joint as the needle approaches the exterior surface of the tissue;

wherein an arthroscope is used to observe the interior surface of the tissue from the interior of the joint as the needle approaches the exterior surface of the tissue.

31. A method according to claim 30 wherein the tissue comprises a capsule.

32. A method according to claim 30 wherein the hollow needle comprises a distal end, a proximal end and a lumen extending between the distal end and the proximal end, and further wherein the light-emitting needle assembly comprises a light unit at least partially disposed within the lumen of the hollow needle.

33. A method according to claim 32 wherein the light unit comprises a light fiber comprising a distal end and a proximal end, and further wherein the light fiber is at least partially disposed within the lumen of the hollow needle.

34. A method according to claim 32 wherein the light unit comprises a handle, and further wherein the handle is releasably securable to the hollow needle.

35. A method according to claim 33 wherein the distal end of the light fiber is disposed adjacent to the distal end of the hollow needle.

36. A method according to claim 35 wherein the distal end of the light fiber acts as an obturator for the distal end of the hollow needle so as to prevent tissue coring.

37. A method according to claim 33 wherein the light unit further comprises a light-emitting element disposed adjacent to the proximal end of the light fiber, such that light from the light-emitting element enters the proximal end of the light fiber and is emitted from the distal end of the light fiber.

38. A method according to claim 37 wherein the light-emitting element comprises an LED.

39. A method according to claim 37 wherein the light-emitting element emits light having a wavelength in at least one of the infrared (IR) and near-infrared (near-IR) wavelengths.

40. A method according to claim 30 wherein the orientation of the hollow needle approaching the exterior surface of the tissue is modified as the hollow needle approaches the exterior surface of the tissue based upon observation of the light emitted from the distal end of the light-emitting needle assembly.

41. A method according to claim 40 wherein, after the light-emitting needle assembly has advanced through the tissue, the light source is removed from the light-emitting needle assembly without removing the hollow needle from the tissue.

42. A method according to claim 41 comprising the steps of:
removing the light source from tissue;
placing a guidewire through the hollow needle;
removing the hollow needle from the tissue;
advancing a cannulated device over the guidewire; and
removing the guidewire from the cannulated device.

43. A method for accessing the interior of a joint, wherein the joint comprises tissue which defines a boundary of the joint, the tissue comprising an interior surface facing toward the interior of the joint and an exterior surface facing away from the interior of the joint, the method comprising:

providing a light-emitting needle assembly comprising a hollow needle having a light source at the distal end thereof; and observing the interior surface of the tissue from the interior of the joint as the needle approaches the exterior surface of the tissue;

wherein the orientation of the needle approaching the exterior surface of the tissue is modified as the needle approaches the exterior surface of the tissue based upon observation of the light source at the distal end of the light-emitting needle assembly;

wherein, after the light-emitting needle assembly has advanced through the tissue, the light source is removed from the light-emitting needle assembly without removing the needle from the tissue.

44. A method according to claim 43 comprising the steps of:
removing the light-emitting needle assembly from tissue;
placing a guidewire through the needle;
removing the needle from the tissue;
advancing a cannulated device over the guidewire; and
removing the guidewire from the cannulated device.

45. A method according to claim 43 wherein the tissue comprises a capsule.

46. A method according to claim 43 wherein the hollow needle comprises a distal end, a proximal end and a lumen extending between the distal end and the proximal end, and further wherein the light-emitting needle assembly comprises a light unit at least partially disposed within the lumen of the hollow needle.

47. A method according to claim 46 wherein the light unit comprises a light fiber comprising a distal end and a proximal end, and further wherein the light fiber is at least partially disposed within the lumen of the hollow needle.

48. A method according to claim 46 wherein the light unit comprises a handle, and further wherein the handle is releasably securable to the hollow needle.

49. A method according to claim 47 wherein the distal end of the light fiber is disposed adjacent to the distal end of the hollow needle.

50. A method according to claim 49 wherein the distal end of the light fiber acts as an obturator for the distal end of the hollow needle so as to prevent tissue coring.

51. A method according to claim 47 wherein the light unit further comprises a light-emitting element disposed adjacent to the proximal end of the light fiber, such that light from the light-emitting element enters the proximal end of the light fiber and is emitted from the distal end of the light fiber.

52. A method according to claim 51 wherein the light-emitting element comprises an LED.

53. A method according to claim 51 wherein the light-emitting element emits light having a wavelength in at least one of the infrared (IR) and near-infrared (near-IR) wavelengths.

54. A method according to claim 43 wherein an arthroscope is used to observe the interior surface of the tissue from the interior of the joint as the hollow needle approaches the exterior surface of the tissue.

* * * * *